(12) United States Patent  (10) Patent No.: US 10,159,792 B2
Nowak  (45) Date of Patent: Dec. 25, 2018

(54) DRUG ADMINISTERING DEVICE AND ASSEMBLY METHOD THEREFOR

(71) Applicant: BRITANNIA PHARMACEUTICALS LTD., Reading (GB)

(72) Inventor: Rachael Nowak, Alfold (GB)

(73) Assignee: BRITANNIA PHARMACEUTICALS LTD., Berkshire (GB)

( * ) Notice: Subject to any disclaimer, the term of this patent is extended or adjusted under 35 U.S.C. 154(b) by 0 days.

(21) Appl. No.: 14/787,896

(22) PCT Filed: Apr. 25, 2014

(86) PCT No.: PCT/EP2014/001107
§ 371 (c)(1),
(2) Date: Oct. 29, 2015

(87) PCT Pub. No.: WO2014/177260
PCT Pub. Date: Nov. 6, 2014

(65) Prior Publication Data
US 2016/0106922 A1    Apr. 21, 2016

(30) Foreign Application Priority Data

Apr. 30, 2013  (DE) .................. 10 2013 007 389

(51) Int. Cl.
*A61M 5/24*  (2006.01)
*A61M 5/20*  (2006.01)
*A61M 5/315*  (2006.01)

(52) U.S. Cl.
CPC .......... *A61M 5/24* (2013.01); *A61M 5/31533* (2013.01); *A61M 5/20* (2013.01);
(Continued)

(58) Field of Classification Search
CPC ...... A61M 5/24; A61M 5/31533; A61M 5/20; A61M 5/31546; A61M 2005/2407;
(Continued)

(56) References Cited

U.S. PATENT DOCUMENTS 8,968,257 B2 *  3/2015  Dasbach ................. A61M 5/24
                                                604/186
2002/0052578 A1 *  5/2002  Moller .................... A61M 5/24
                                                604/208
(Continued)

FOREIGN PATENT DOCUMENTS

DE       102005063497 B4    9/2009
DE    102013007389.8 A1    10/2014
(Continued)

*Primary Examiner* — Nathan R Price
*Assistant Examiner* — Dung Ulsh
(74) *Attorney, Agent, or Firm* — Thrive IP; Bernard Klosowski

(57) ABSTRACT

The present disclosure refers to drug administering devices that may include a casing front portion in which a cavity is formed and which includes front connecting means, a drug container received in the cavity, a casing rear portion comprising a piston rod which is displaceable into the cavity, and rear connecting means for releasably connecting to the front connecting means, wherein said casing front portion comprises at least two members which, in locking engagement with each other, delimit a front portion of the cavity and a rear portion having a cross section which is narrower than that of the front portion and too narrow for the drug container to pass.

11 Claims, 4 Drawing Sheets

(52) U.S. Cl.
CPC . *A61M 5/31546* (2013.01); *A61M 2005/2407* (2013.01); *A61M 2005/2437* (2013.01); *A61M 2005/2488* (2013.01); *A61M 2205/52* (2013.01); *A61M 2205/6045* (2013.01); *A61M 2207/00* (2013.01)

(58) Field of Classification Search
CPC .. A61M 2005/2437; A61M 2005/2488; A61M 2205/52; A61M 2205/6045
See application file for complete search history.

(56) References Cited

U.S. PATENT DOCUMENTS

| | | | |
|---|---|---|---|
| 2005/0137571 A1 | 6/2005 | Hommann | |
| 2006/0153693 A1* | 7/2006 | Fiechter | A61M 5/31553 417/63 |
| 2007/0021715 A1* | 1/2007 | Kohlbrenner | A61M 5/20 604/67 |
| 2008/0262436 A1* | 10/2008 | Olson | A61M 5/2033 604/198 |
| 2009/0069753 A1* | 3/2009 | Ruan | A61M 5/3202 604/192 |
| 2009/0247951 A1* | 10/2009 | Kohlbrenner | A61M 5/20 604/134 |
| 2009/0259197 A1* | 10/2009 | Christiansen | A61M 5/24 604/208 |
| 2009/0270804 A1* | 10/2009 | Mesa | A61M 5/2033 604/111 |
| 2010/0036320 A1* | 2/2010 | Cox | A61M 5/31593 604/135 |
| 2010/0106099 A1* | 4/2010 | Christiansen | A61M 5/3129 604/208 |
| 2010/0152672 A1* | 6/2010 | Raab | A61M 5/31555 604/208 |
| 2011/0046565 A1* | 2/2011 | Radmer | A61M 5/20 604/211 |
| 2011/0054412 A1* | 3/2011 | Eich | A61M 5/20 604/207 |
| 2011/0152781 A1* | 6/2011 | Brunnberg | A61M 5/3129 604/189 |
| 2011/0257602 A1* | 10/2011 | Watanabe | A61J 7/0472 604/189 |
| 2012/0095412 A1* | 4/2012 | Schabbach | A61M 5/31505 604/211 |
| 2012/0136317 A1 | 5/2012 | Teucher et al. | |
| 2012/0165747 A1* | 6/2012 | Lanin | A61M 5/14244 604/207 |
| 2012/0197207 A1* | 8/2012 | Stefanski | A61M 5/20 604/189 |
| 2012/0283658 A1* | 11/2012 | Plumptre | A61M 5/24 604/211 |
| 2012/0296276 A1* | 11/2012 | Nicholls | A61M 5/31501 604/110 |
| 2013/0068319 A1* | 3/2013 | Plumptre | A61M 5/24 137/315.01 |
| 2013/0079718 A1* | 3/2013 | Shang | A61M 5/20 604/131 |
| 2013/0211327 A1* | 8/2013 | Osman | A61M 5/24 604/111 |
| 2013/0303985 A1* | 11/2013 | Wotton | A61M 37/00 604/115 |
| 2014/0323978 A1* | 10/2014 | Henley | A61M 5/2033 604/198 |

FOREIGN PATENT DOCUMENTS

| | | |
|---|---|---|
| WO | 2011/051366 A2 | 5/2011 |
| WO | 2011/089207 A2 | 7/2011 |
| WO | 2011/131775 A1 | 10/2011 |
| WO | 2011/131776 A1 | 10/2011 |
| WO | 2012/017035 A1 | 2/2012 |
| WO | 2012/152667 A1 | 11/2012 |
| WO | 2014/177260 A1 | 11/2014 |

* cited by examiner

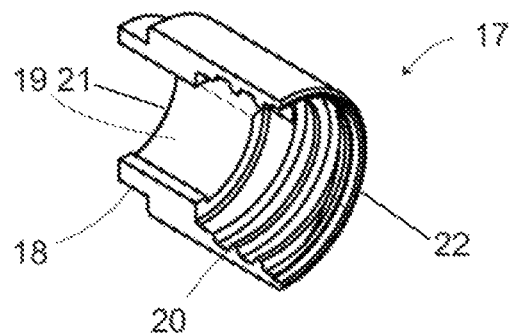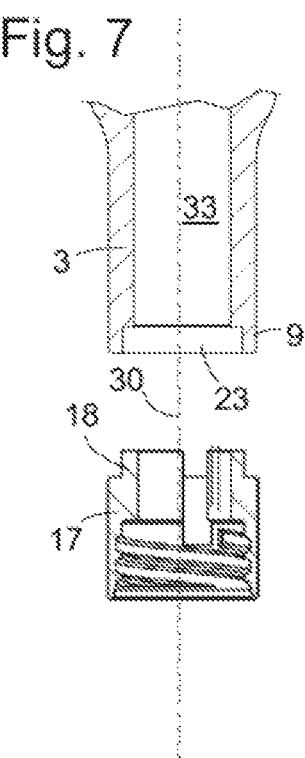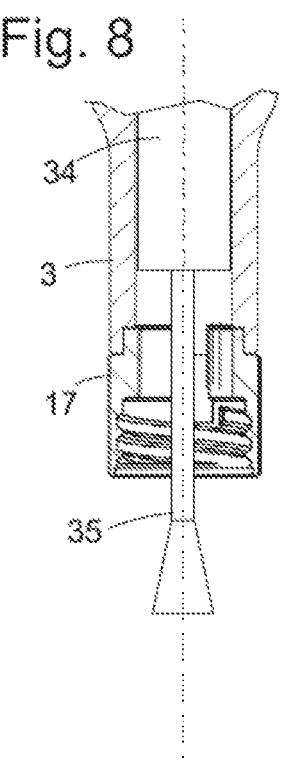

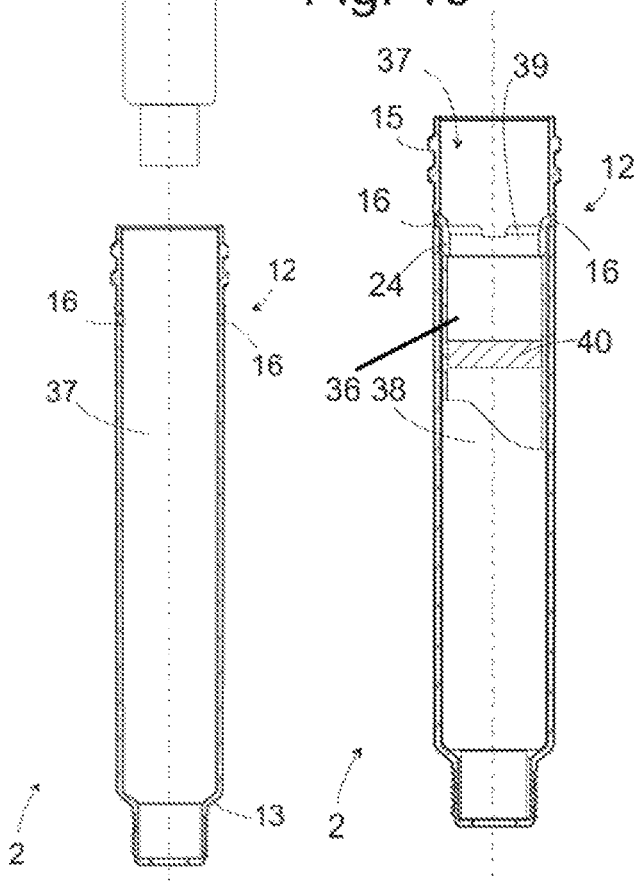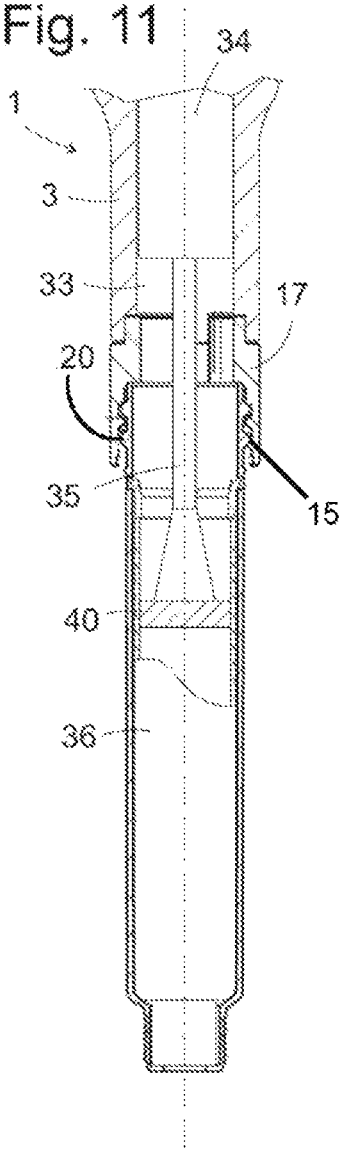

DRUG ADMINISTERING DEVICE AND ASSEMBLY METHOD THEREFOR

FIELD

The present disclosure relates to a drug administering device, in particular to a device for repeatedly administering doses of a given drug from a same drug container and a method for assembly of such a device.

BACKGROUND

Devices have become very popular for self-administration of certain drugs such as insulin or apomorphine by patients.

A conventional device of this type is known e.g. from US 2005/0137571 A1. This device has a casing divided into front and rear portions which form front and rear parts, respectively, of a cavity in which a drug container is accommodated, and which can be taken apart in order to replace the drug container when empty.

Since the machinery needed for producing the drug containers and for filling them in a sterile manner is expensive, pharmaceutics manufacturers tend to use a same type of drug container for different drugs or for different preparations of a same drug.

If a patient uses such different drugs or different preparations, he might inadvertently replace an empty drug container by a container of a different drug or a different preparation, and consequently administer to himself a wrong dose of a required drug or even the wrong drug.

SUMMARY

The present disclosure aims at eliminating the possibility of administering the wrong drug or dosage.

According to an embodiment of the disclosure, a drug administering device may include:

a casing front portion in which a cavity is formed and which comprises front connecting means, a drug container received in the cavity, a casing rear portion comprising a piston rod which is displaceable into the cavity, and rear connecting means for releasably connecting to the front connecting means, wherein the casing front portion comprises at least two members which, in locking engagement which each other, delimit a front portion of the cavity and a rear portion the cross section of which is narrower than that of the front portion and too narrow for the drug container to pass.

Due to the narrow cross section of the cavity rear portion, a drug container received in the cavity front portion cannot be removed without taking apart the members of the casing front portion. Due to the locking engagement, the two members of the casing front portion cannot be separated from one another without being damaged. Therefore, a drug container which has been placed in the front portion of the cavity by a drug manufacturer cannot be removed by the patient in a way which would allow the casing front portion to be re-used with another drug container. When the drug container installed in such a casing front portion by the manufacturer is empty, the patient must replace the casing front portion along with the drug container.

Further, securing the drug container within the casing front portion by bringing the members into locking engagement has the advantage that the use of glue for fixing the drug container can be avoided completely. There is no risk, therefore, that the drug container might be stuck to the casing front portion in a position in which its contents cannot be injected. Rather, if not placed correctly, the drug container will prevent the members from engaging each other. Since glue is not used, there is no possibility of solvent from the glue contaminating the drug.

While the container, for the economical reasons presented above, tends to have a same shape for different types of drugs or preparations, no such restraint exists for the casing front portion. The casing front portion can therefore come in a variety of shapes or colors, which a patient is unlikely to confuse. More importantly, the type of connecting means can vary depending on the type of drug or drug preparation contained in the casing front portion. If each type of drug or drug preparation has specific connecting means associated to it, and if a drug container is empty and is discarded along with its casing front portion, it can only be replaced by a casing front portion having the same type of front connecting means, matching the rear connecting means of the casing rear portion. Therefore, it is practically impossible to combine a drug container with a casing rear portion for which it is not specified.

Since the casing rear portion can be used again and again, an aim of the disclosure is also achieved by a sub-assembly of the drug administering device described above, which does not include the casing rear portion, but may include:

a casing front portion in which a cavity for receiving a drug container is formed and which comprises front connection means for releasably connecting the casing front portion to the casing rear portion, wherein the casing front portion comprises at least two members which, in locking engagement with each other, delimit a front portion of the cavity and a rear portion having a narrower cross section than the front portion, and a drug container received in the front portion of the cavity and having a piston facing the rear portion of the cavity, in order to be engaged by a piston rod of the casing rear portion, when connected to the casing front portion.

The first one of the two members of the casing front portion may be tubular, and the rear portion of the cavity is formed by a second of the members being inserted into a rear end of the tubular first member.

In order to achieve a tight fit within the tubular first member and to allow the passage of the piston rod, the second member preferably is ring-shaped, and the piston rod is displaceable through the ring-shaped second member.

For locking the second member within the first one, the second member can have an outer surface facing an inner wall surface of the tubular first member, and at least one locking boss of that second member projects beyond the outer surface and engages a cutout of the inner wall surface. preferably, there are two locking bosses at a minimum.

When the second member has a ring portion, the locking boss is preferably formed on a tab which protrudes from the ring portion in an axial direction thereof. While the ring portion is extremely hard to compress in the radial direction, the tab may yield radially when the second member is inserted into the tubular first member, and may resiliently engage the cutout when the second member reaches its target position.

The locking boss may have a forward facet which is which is slanted in a direction of the insertion. Such a facet facilitates a displacement of the locking boss in the radial direction when the second member is beginning to be inserted in the first member.

A rearward facet of the locking boss should be substantially perpendicular to the direction of insertion, in order to ensure locking engagement of the two members when the second member has reached its target position.

The front connecting means might be formed on either member of the casing front portion. Preferably, it is formed on the first member, so that the second member may be concealed completely within the first when casing front and rear portions are connected to each other.

Preferably, the front and rear connecting means are threads. These may be provided in left- or right-handed form, with different cross sectional shapes, leads and pitches, so that a specific type of thread may be provided for a large variety of drugs or drug preparations, ensuring that a specific casing rear portion can only be used for the drug preparation for which it was certified.

In order to enable cost-effective manufacture of a large variety of drug-specific types of casing rear portion, the casing rear portion may include a main assembly in which the piston rod is mounted and which includes a dosing mechanism for controlling displacement of the piston rod, and an adapter member in which the rear connecting means is formed. Such an adapter member may be connected to the main assembly e.g. by gluing or welding.

An aim of the disclosure is also achieved by a method for assembling at least a sub-assembly of the drug administering device describe above, including:

providing the at least two members of the casing front portion and the drug container, joining the drug container to the first member, forming the cavity receiving the drug container by connecting the first and second members.

The drug administering device may be completed by the manufacturer of the sub-assembly, by joining the sub-assembly to the casing rear portion. Alternatively, a patient, having emptied the drug container of the administering device used by him, may detach the casing rear portion of the device and combine it with a new sub-assembly comprising a full drug container.

BRIEF DESCRIPTION OF THE DRAWINGS

Further features and advantages of the disclosure will become apparent from the subsequent description of embodiments thereof, referring to the appended drawings.

FIG. 6 is a perspective view of an adapter member of a casing rear portion;

FIG. 7 is a sectional view of components of the casing rear portion prior to assembly;

FIG. 8 is a sectional view of the casing rear portion after assembly;

FIG. 9 is a sectional view of components of the casing front portion before assembly;

FIG. 10 is a sectional view of the casing front portion after assembly; and

FIG. 11 is a sectional view of the device with casing front and rear portions connected to each other.

DETAILED DESCRIPTION OF THE DRAWINGS

Detailed reference will now be made to the drawings in which examples embodying the present disclosure are shown. The detailed description uses numerical and letter designations to refer to features of the drawings.

The drawings and enabling description provide a full and enabling description of the disclosure and of a manner and process of making and using it. Each embodiment is provided by way of explanation of the subject matter and are not meant as limitations thereof. In fact, it will be apparent to those skilled in the art that modifications can be made to the described embodiments and therefore, that the specification is broader in scope than the exemplary embodiments discussed herein.

Figure 1:
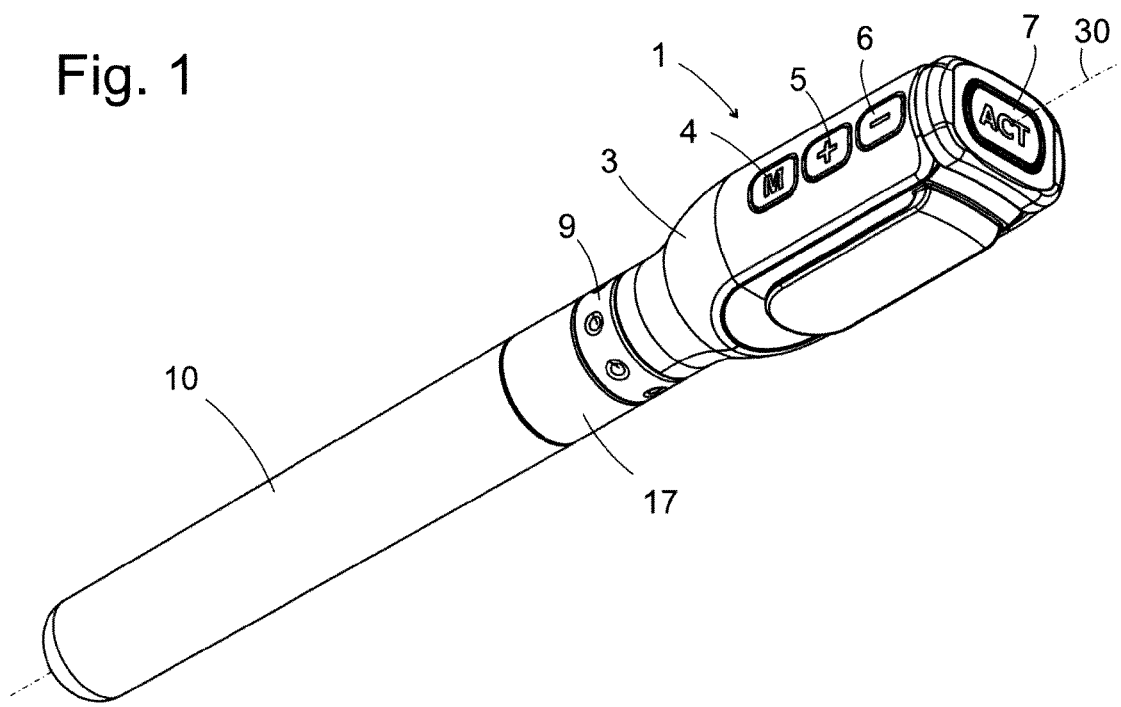
FIG. 1 is a perspective view of a drug administering device in a closed configuration.

FIG. 1 is a perspective view of a drug administering device according to the present disclosure. The device is similar to a pen in that its overall shape is elongate and can be assigned a longitudinal axis 30. A casing portion referred to here as casing rear portion 1 because it faces away from a patient's skin when administering a drug, comprises a casing member 3 in which a dosing mechanism, not shown in FIG. 1, is accommodated.

Figure 2:
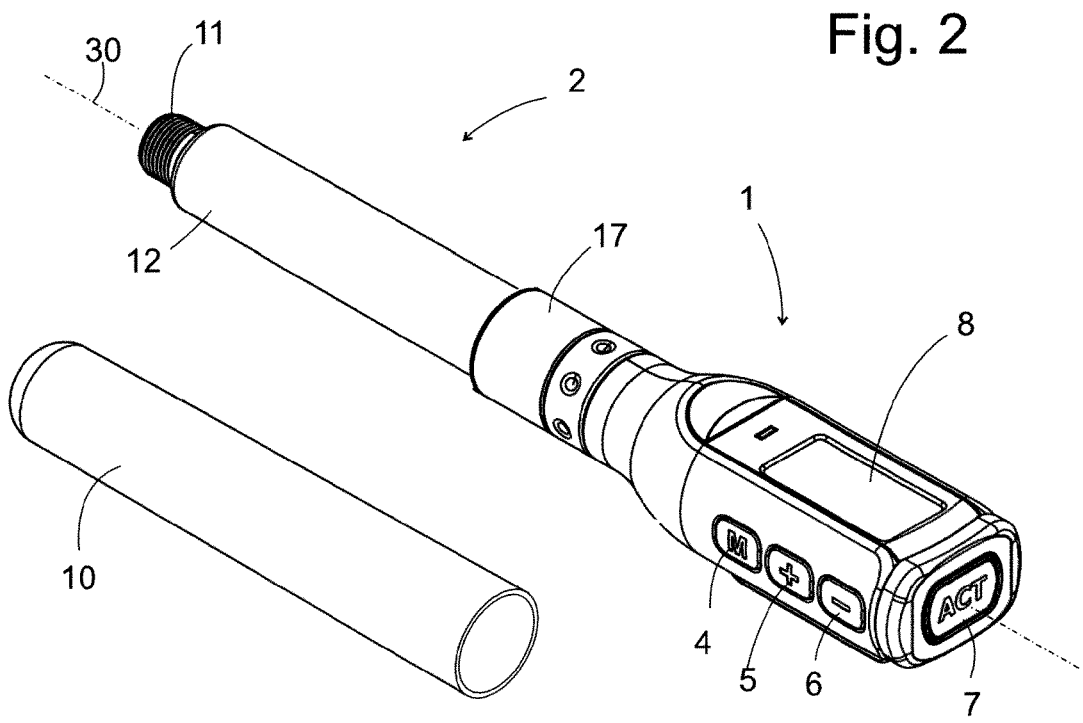
FIG. 2 is a perspective view of the device as in FIG. 1 with its cap removed.

The casing member 3 may include a clip for attaching the device e.g. to a garment. Buttons 4, 5, 6, 7 may be provided for controlling operation of the dosing mechanism, e.g. a button 4 for retrieving a previously administered dose from an electronic memory of the device, buttons 5, 6 for increasing or decreasing, respectively, the dose to be administered, and a button 7 for triggering injection of the dose. As can be seen in FIG. 2, a display 8 may be provided for displaying the dose set by manipulating buttons 4, 5, 6. Additionally or as an alternative to dose setting buttons 4, 5 6, a rotatable ring 9 or some other kind of displaceable member may be provided on casing rear portion 1, which is connected the dosing mechanism inside casing rear portion 1 for controlling the dose to be injected.

In FIG. 1, a removable cap 10 is concealing a casing front portion 2 of the device. In FIG. 2, the cap 10 is removed, and casing front portion 2 is shown. At the foremost tip of front portion 2, there is a thread 11 which, when in use, holds an injection needle, not shown in FIG. 2.

Figure 3:
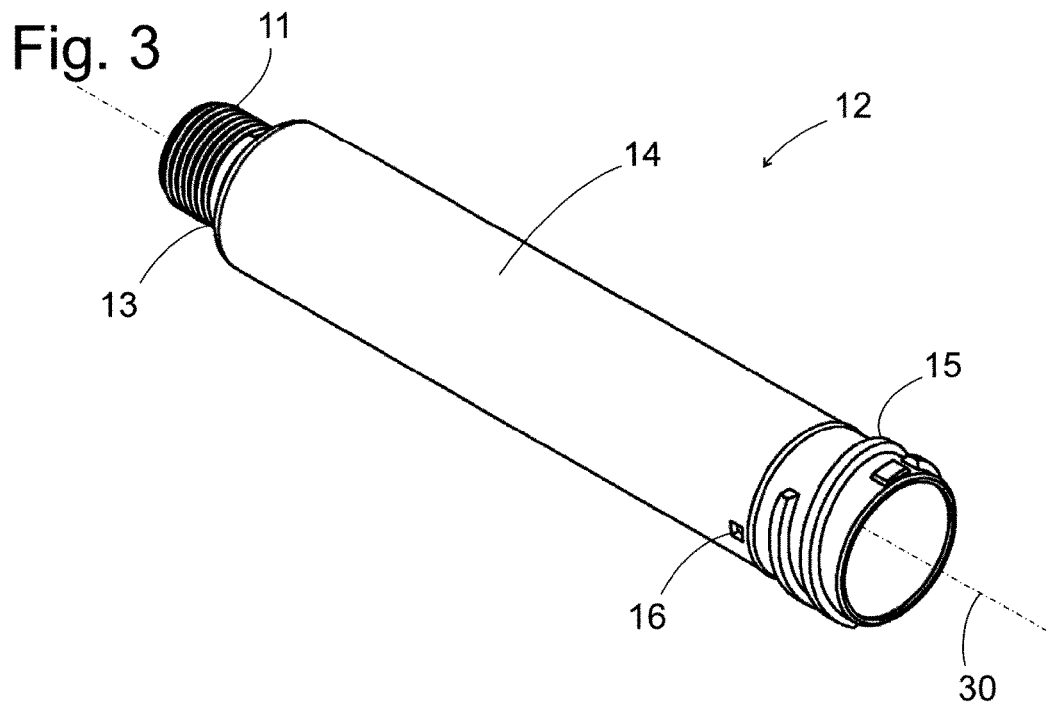
FIG. 3 is a perspective view of a tubular member of a casing front portion of the device.

FIG. 3 is a perspective view of a tubular member 12 of casing front portion 2 according to an embodiment of the disclosure. The tubular member 12 is injection-molded in one piece from plastic, e.g. from ABS. It comprises the thread 11, a tapering portion 13 and a hollow cylindrical portion 14. A male thread 15 is formed on the outside of cylindrical portion 14 adjacent to its rearward end, facing the viewer in FIG. 3. Next to thread 15, two diametrically opposed holes 16 are formed in tubular member 12, one of which is shown in FIG. 3.

Figure 4:
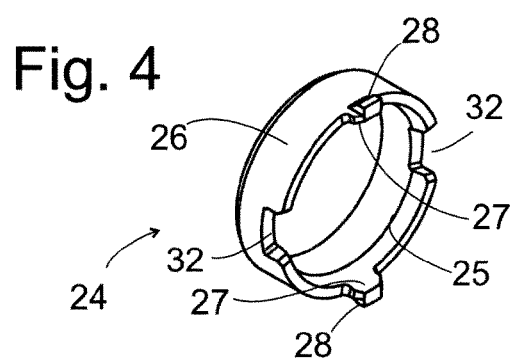
FIG. 4 is a perspective view of an annular retaining member of the casing front portion.
Figure 5:
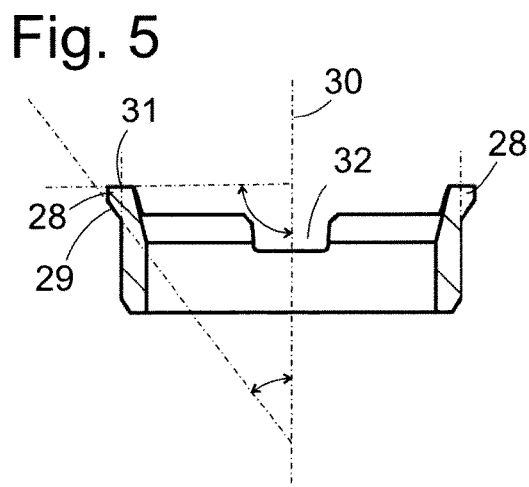
FIG. 5 is a cross section of the retainer member.

FIG. 4 illustrates a retaining member 24 of casing front portion 2. Retaining member 24 has a ring shaped body 25 with a cylindrical outer surface 26. At a rear side of body 25, two tabs 27 extend in the axial direction and carry locking bosses 28 which project beyond the outer surface 26 in the radial direction. As shown in FIG. 5 in an enlarged section, each boss 28 has a front facet 29 extending in a plane which intersects the axis 30 at a pointed angle α of less than 45°. A rear facet 31 extends in a plane which intersects axis 30 at an angle β larger than α. The angle β may be a right angle. Two notches 32 are formed at diametrically opposite locations of the rear side of body 25.

FIG. 6 is a perspective section view of an adapter member 17 of casing rear portion 1. On the outside, the adapter member 17 is cylindrical. At its rear end, a projection 18 of reduced diameter is formed. In FIG. 6, the adapter member 17 is shown cut open along a plane extending in its axial direction, in order to show a passage 19 extending through it. In a front portion 22 of passage 19, a female thread 20 is formed which matches the thread 15 of tubular member 12. A rear portion 21 of passage 19 has no thread formed in it and is narrower than threaded front portion 22.

FIG. 7 is an exploded section view of casing member 3 and adapter member 17 of the casing rear portion 1. Casing member 3 has a recess 23 which mates projection 18 of adapter member 17 and a cavity 33 extending from recess 23 along axis 30. An outer wall of recess 23 might be formed by ring 9.

During the assembly of casing rear portion 1 and as shown in FIG. 8, the dosing mechanism mentioned above, referred to here by reference numeral 34, is inserted into cavity 32. Dosing mechanism 34 carries a piston rod 35 and controls its displacement. When adapter member 17 is fixed to casing member 3, e.g. by gluing or welding, piston rod 35 extends through it.

FIG. 9 shows tubular member 12, a drug container 36 and retaining member 24 prior to assembly. In a first step of the assembly process, drug container 36 is slid into a cavity 37 of tubular member 12 until it abuts against its tapering portion 13. The retaining member 24 is then pushed into tubular member 12 until it abuts against drug container 36. Due to the inclination of the front facets 29, the tabs 27 of retaining member 24 are resiliently displaced towards axis 30 upon entry into tubular member 12 and relax into holes 16 when retaining member 24 has reached a target position in contact with drug container 36.

There is a possibility that when the retaining member 24 abuts against drug container 36, the bosses 28 are displaced with respect to the holes 16 in the circumferential direction, and it may be necessary to rotate retaining member 24 around axis 30 in order to have the bosses 28 engage into the holes 16. The torque necessary for this may be applied by a blade-type tool, e.g. a screwdriver, engaging the notches 32 of retaining member 24.

FIG. 10 shows the retaining member 24 locked to tubular member 12 by the bosses 28 engaging holes 16. It is readily appreciated when the retaining member 24 is inserted into tubular member 12, it defines a front portion 38 of cavity 37, having a large enough diameter to accommodate drug container 36, and a rear portion 39, namely the passage through its body 25, which is too narrow for the drug container 36 to pass, so that drug container is locked in the position shown in FIG. 10.

If the drug container 36 was not placed correctly within cavity 37, but was e.g. stuck in tubular member 12 without reaching tapered portion 13, it is easily seen from FIG. 10 that retaining member 24 would not be able to lock in tubular member 12.

Due to the rear facets 31 being substantially perpendicular to axis 30, it is practically not possible to remove the retaining member 24 without breaking its tabs 27, eroding the bosses 28 or inflicting some other damage to casing front portion 2 that prevents it re-use.

In FIG. 11, the casing rear portion of

FIGS. 7, 8 and the casing front portion of FIGS. 9, are screwed together. Drug container 36 is partly shown in section here, so that piston rod 35 is seen to be in contact with a piston 40 of drug container 36.

Upon actuation of button 7 by the user, the dosing mechanism 34 advances piston rod 35, thereby displacing piston 40 and ejecting liquid drug preparation from container 36. The ejected volume is directly proportional to an amount of drug set by the user by means of buttons 4, 5, 6, but the amount of drug dispensed will only correspond to the set amount if the proportionality factor is adapted to the drug in container 36 and its concentration. Therefore, the casing rear portion 1 should be used with one drug and one concentration, as specified by its manufacturer.

Drug containers 36 may come in various types which differ not by their shapes but by the drugs contained in them and/or their concentration.

When a drug manufacturer assembles drug containers 36 and casing front portions 2, a tubular member 12 having a different type of thread 15 should be used for each type of container 36. Since a given type of male thread 15 of the tubular member 12 matches with only one type of female thread 20 of an adapter member 17, it can be ensured that a casing front portion 2 and the drug container 36 installed therein can only be combined with a casing rear portion 1 having a dosing mechanism 34 adapted to the type of drug in container 36 and to its concentration. In this way, patients can be reliably prevented from administering themselves a wrong type of drug or a wrong dose.

For a patient who uses two or more dispensing devices for administering himself different drugs, using the administering device could be made still more convenient if each type of drug had associated to it not only specific type of threads 15, 20, but also a specific colour of at least part of casing rear and front portions 1, 2. Specifically, if the tubular member 12 and a matching adapter member 17 have the same colour, the patient can tell without trying, just by looking at separate casing front and rear portions, whether it will be possible to combine them or not.

As previously stated, detailed embodiments of the present disclosure are disclosed herein; however, the disclosed embodiments are merely examples that may be embodied in various forms. Those skilled in the art will appreciate and understand that many modifications and other variations stand within the intended scope of the disclosure. Furthermore, the foregoing description of various embodiments does not necessarily imply exclusion. For example, "some" embodiments may include all or part of "other" and "further" embodiments within the scope of the disclosure. In addition, "a" does not mean "one and only one;" "a" can mean "one and more than one."

The invention claimed is:

1. A drug administering device comprising:
a casing front portion in which a cavity is formed therein and which comprises front connecting means for releasable connection;
a drug container received in said cavity;
a casing rear portion comprising a piston rod which is displaceable into said cavity; and
rear connecting means for releasably connecting to said front connecting means, wherein said casing front portion comprises at least two members which, in locking engagement with each other, delimit a front portion of said cavity and a rear portion, a cross section of the rear portion being narrower than that of the front portion and too narrow for the drug container to pass, wherein the two members in locking engagement cannot be separated from one another without being damaged; wherein a first one of said two members is tubular, and the rear portion of said cavity is formed by a second one of said members being inserted into a rear end of said first member.

2. The drug administering device of claim 1, wherein the second member is ring-shaped and the piston rod is displaceable through said second member.

3. The drug administering device of claim 1, wherein the second member has an outer surface facing an inner wall surface of said first member and at least one locking boss of said second member projects beyond said outer surface and engages a cutout of said inner wall surface.

4. The drug administering device of claim 3, wherein the second member has an annular body and the locking boss is formed on a tab which protrudes from said annular body in an axial direction thereof.

5. The drug administering device of claim 3, wherein the locking boss has a forward facet which is slanted in a direction of insertion.

6. The drug administering device of claim 3, wherein the locking boss has a rearward facet which is substantially perpendicular to a direction of insertion.

7. The drug administering device of claim 1, wherein the front connecting means is formed on said first member.

8. The drug administering device of claim 1, wherein the front and rear connecting means are threads.

9. The drug administering device of claim 1, wherein the casing rear portion comprises a casing member in which the piston rod is mounted and which accommodates a dosing mechanism for controlling displacement of the piston rod, and an adapter member in which the rear connecting means is formed.

10. The drug administering device of claim 1, wherein the drug container comprises a piston which co-operates with the piston rod.

11. A method for assembling the drug administering device of claim 1, comprising:
   providing said at least two members of the casing front portion and the drug container;
   joining the drug container to said first member; and
   forming the cavity receiving the drug container by connecting said first and second members.

* * * * *